United States Patent
Sasaki

(10) Patent No.: US 10,960,336 B2
(45) Date of Patent: Mar. 30, 2021

(54) MEDICAL ELECTRONIC APPARATUS

(71) Applicant: Sony Olympus Medical Solutions Inc., Tokyo (JP)

(72) Inventor: Toshiyuki Sasaki, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 221 days.

(21) Appl. No.: 15/904,538

(22) Filed: Feb. 26, 2018

(65) Prior Publication Data
US 2018/0280855 A1     Oct. 4, 2018

(30) Foreign Application Priority Data

Mar. 28, 2017 (JP) ............................. JP2017-063901

(51) Int. Cl.
| | |
|---|---|
| *B01D 46/00* | (2006.01) |
| *G01N 15/08* | (2006.01) |
| *A61B 90/20* | (2016.01) |
| *H05K 7/20* | (2006.01) |
| *A61B 90/00* | (2016.01) |

(52) U.S. Cl.
CPC .......... *B01D 46/0047* (2013.01); *A61B 90/00* (2016.02); *A61B 90/20* (2016.02); *B01D 46/0065* (2013.01); *G01N 15/082* (2013.01); *H05K 7/20181* (2013.01); *B01D 46/0086* (2013.01); *B01D 2279/35* (2013.01); *B01D 2279/45* (2013.01); *G01N 2015/084* (2013.01)

(58) Field of Classification Search
CPC ............ B01D 2279/35; B01D 2279/45; B01D 46/0086; B01D 46/0047; B01D 46/0065; G01N 15/082
See application file for complete search history.

(56) References Cited

U.S. PATENT DOCUMENTS

| | | | | |
|---|---|---|---|---|
| 2,203,766 | A * | 6/1940 | Baer ...................... | G01F 23/36 73/313 |
| 3,768,087 | A * | 10/1973 | Kaye ..................... | G08B 13/08 340/545.2 |
| 3,965,928 | A * | 6/1976 | Siegwart ................ | F16K 17/30 137/499 |
| 4,559,518 | A * | 12/1985 | Latta, Jr. ................ | B60Q 1/50 116/28 R |

(Continued)

FOREIGN PATENT DOCUMENTS

| | | | | |
|---|---|---|---|---|
| JP | S59-28289 U | | 2/1984 | |
| JP | 60046422 A * | | 3/1985 | ............ G01F 23/32 |

(Continued)

OTHER PUBLICATIONS

Office Action dated Dec. 8, 2020, in corresponding Japanese patent Application No. 2017-063901, 10 pages.

*Primary Examiner* — John Fitzgerald

(74) *Attorney, Agent, or Firm* — Xsensus, LLP

(57) ABSTRACT

A medical electronic apparatus includes: a casing including a lid portion provided with: a first inlet duct; a second inlet duct; and an outlet duct, the lid portion being configured to open the second inlet duct when the first inlet duct is blocked; a detection unit configured to detect an open/close state of the lid portion; and an output unit configured to output information regarding blockage of the first inlet duct based on a detection result of the detection unit.

19 Claims, 6 Drawing Sheets

(56) References Cited

U.S. PATENT DOCUMENTS

| | | | | |
|---|---|---|---|---|
| 5,018,304 | A * | 5/1991 | Longoria | E05F 15/63 49/26 |
| 5,438,981 | A * | 8/1995 | Starr | A61M 16/208 128/205.24 |
| 5,647,355 | A * | 7/1997 | Starr | A61M 16/208 128/205.24 |
| 5,672,103 | A * | 9/1997 | Jardinier | F24F 11/72 454/256 |
| 7,201,052 | B2 * | 4/2007 | Lee | G01F 23/38 73/317 |
| 7,677,098 | B2 * | 3/2010 | Roth | G01F 23/366 73/313 |
| 7,860,671 | B1 * | 12/2010 | LaCaze | G01F 23/38 702/55 |
| 10,279,296 | B2 * | 5/2019 | Lopez | B01D 46/10 |
| 2003/0041665 | A1 * | 3/2003 | Arias | G01F 23/366 73/317 |
| 2007/0157928 | A1 * | 7/2007 | Pujol | A61M 16/16 128/204.14 |
| 2009/0038395 | A1 * | 2/2009 | Roth | G01F 23/366 73/313 |
| 2016/0105996 | A1 * | 4/2016 | Schanzenbach | F04D 29/703 415/121.2 |
| 2017/0209822 | A1 * | 7/2017 | Lopez | B01D 46/0039 |

FOREIGN PATENT DOCUMENTS

| | | |
|---|---|---|
| JP | 2003-8272 | 1/2003 |
| JP | 2003-115683 A | 4/2003 |
| JP | 2006-100309 A | 4/2006 |
| JP | 2008-263078 A | 10/2008 |
| JP | 2012-064718 A | 3/2012 |
| JP | 2014-167949 A | 9/2014 |
| JP | 2016-143754 A | 8/2016 |
| WO | 2013/161617 A1 | 10/2013 |

* cited by examiner

MEDICAL ELECTRONIC APPARATUS

CROSS-REFERENCE TO RELATED APPLICATION(S)

The present application claims priority to and incorporates by reference the entire contents of Japanese Patent Application No. 2017-063901 filed in Japan on Mar. 28, 2017.

BACKGROUND

The present disclosure relates to a medical electronic apparatus.

An electronic apparatus provided with electronic parts typically has a mechanism for suctioning and discharging external air in order to cool the electronic parts from which heat is generated during operation. For example, JP 2003-8272 A discusses an electronic apparatus provided with a cooling fan, a dustproof filter provided in an inlet duct, an emergency preliminary filter, and a partitioning board pressed by a spring to an inner surface of the preliminary filter. In this technique, when clogging of the filter is progressed, and a pressure loss is generated over a critical range, the partition board moves inward of the apparatus to allow the air to flow to the inside through the preliminary filter to maintain cooling of the electronic parts. In this technique, movement of the partitioning board inward of the apparatus is detected, and a warning is output.

A surface of the medical electronic apparatus may be covered by a cover such as a cover cloth or drape in order to prevent contamination caused by intrusion of drugs or liquid into the inside of the apparatus in some cases. When the cover blocks the inlet duct, cooling of the electronic parts using the air is hindered, and a temperature of the inside of the apparatus increases, so that a trouble may occur. In order to address such a problem, it is conceived that control may be performed such that heat radiation efficiency is improved by increasing the rotation number of the cooling fan when an increase of the internal temperature of the apparatus is detected.

SUMMARY

Since the internal temperature of the apparatus is easily influenced by a surrounding temperature or noise, it is difficult to accurately determine blockage of the inlet duct based on a result of the temperature detection. In addition, it is difficult to set a temperature at which abnormality is determined. If the setting temperature is excessively high, timing may not match even by increasing the heat radiation efficiency of the inside of the apparatus after abnormality determination, and abnormality may occur in the operation. In comparison, if the setting temperature is excessively low, sensitivity of abnormality determination becomes unnecessarily high, so that abnormality may be erroneously determined even in a normal operation state.

In order to address such a problem, it is conceived that the electronic apparatus may be provided with a high-accuracy temperature detection mechanism or a high-performance heat radiation means. However, in this case, the configuration becomes complicated and expensive.

A medical electronic apparatus according to one aspect of the present disclosure may include: a casing including a lid portion provided with: a first inlet duct; a second inlet duct; and an outlet duct, the lid portion being configured to open the second inlet duct when the first inlet duct is blocked; a detection unit configured to detect an open/close state of the lid portion; and an output unit configured to output information regarding blockage of the first inlet duct based on a detection result of the detection unit.

DETAILED DESCRIPTION

Figure 1:
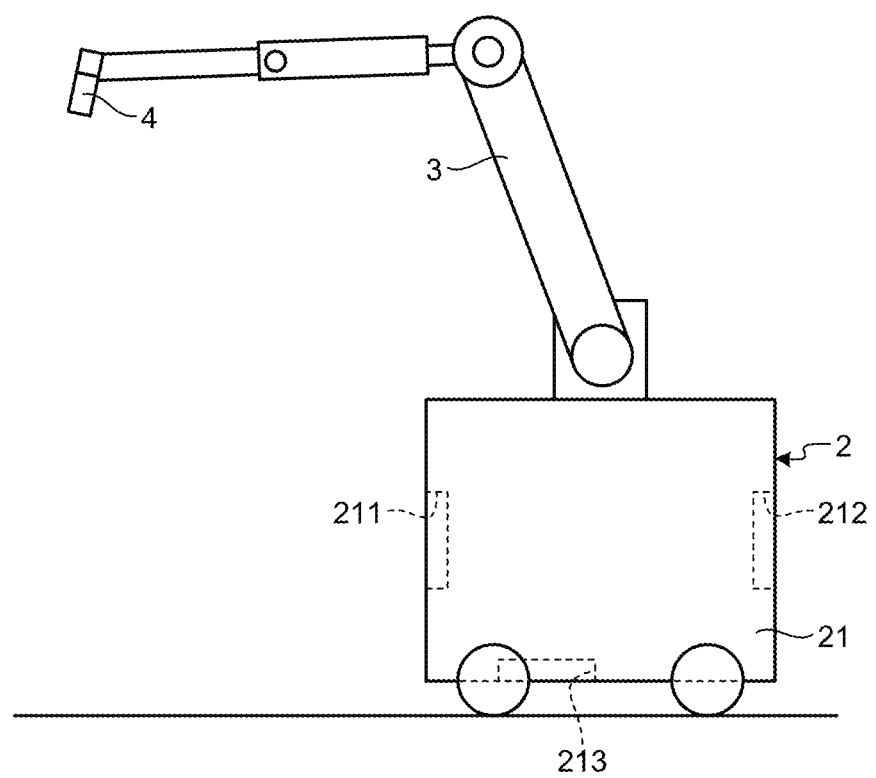
FIG. 1 is a diagram illustrating an exterior configuration of a surgical microscope as a medical electronic apparatus according to a first embodiment.

Embodiments will now be described with reference to the accompanying drawings. Like reference numerals denote like elements throughout the drawings. Note that the drawings are merely for illustrative purposes and may have different dimensions, scales, or the like between some drawings even when the same element is illustrated.

First Embodiment

FIG. 1 is a diagram illustrating an exterior configuration of a surgical microscope as a medical electronic apparatus according to a first embodiment. In FIG. 1, the surgical microscope 1 has a function of magnifying and capturing a microscopic structure of a medical examinee body. The surgical microscope 1 includes a base portion 2 internally provided with various electronic parts, a support portion 3 provided with a plurality of sets of a couple of arm portions and a joint portion that pivotably connects one of the arm portions to the other arm portion and supported by the base portion 2, and a columnar microscope unit 4 provided in a tip of the support portion 3 to capture a magnified image of a microscopic portion of a medical examinee body and create an image signal. The image signal created by the microscope unit 4 is transmitted to the base portion 2 through a transmission cable extending to an internal space of the support portion 3. A control unit (described below) of the base portion 2 creates a display image signal and outputs the image signal to a display device (not illustrated). A user such as a doctor performs operation while viewing the image displayed by the display device.

Figure 2:
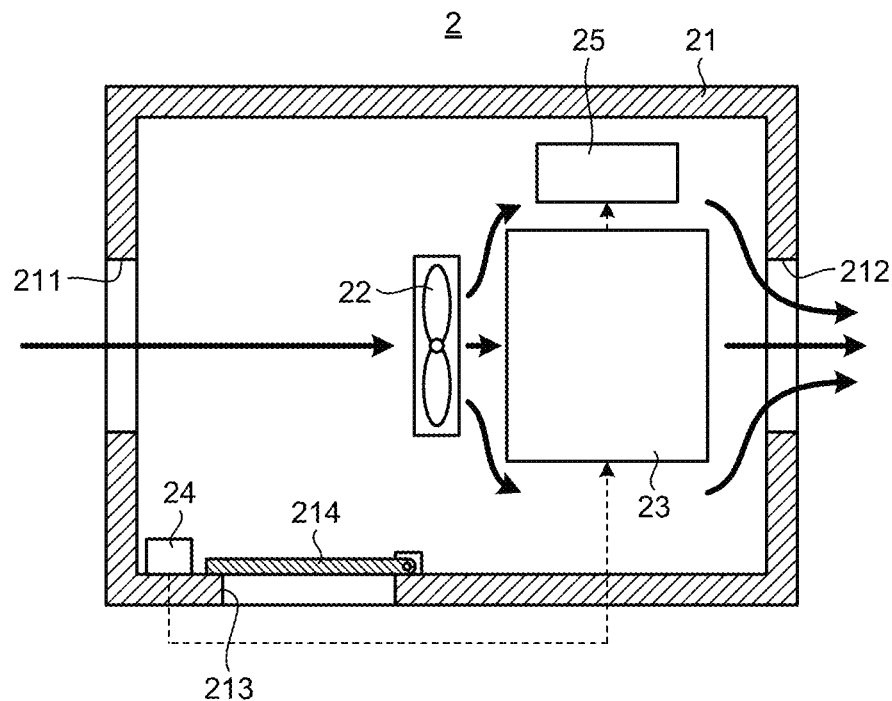
FIG. 2 is a diagram illustrating a schematic internal configuration of a base portion provided in the medical electronic apparatus according to the first embodiment.

FIG. 2 is a diagram illustrating a schematic internal configuration of the base portion 2. The base portion 2 has a casing 21, an air blower 22, a control unit 23, a detection unit 24, and an output unit 25.

The casing 21 has a rectangular shape and includes a first opening 211 as a first inlet duct provided in one of side walls (left side wall of FIG. 2) and a second opening 212 as an outlet duct provided in the other side wall (right side wall in FIG. 2) opposite to the one of the side walls. A third opening 213 as a second inlet duct is provided in a bottom portion (lower portion in FIG. 2) of the casing 21. The side wall where the first opening 211 is provided is a side wall where the microscope unit 4 is placed as illustrated in FIG. 1 and faces a medical examinee body (refer to FIG. 1).

The casing 21 has a lid portion 214 that openably/closably covers the third opening 213 and is opened to allow the third opening 213 to be used as an opening when the first opening 211 is blocked. The lid portion 214 has a structure closed by its self weight in a normal state, and the side where the first opening 211 is placed (left side wall side of FIG. 2) is opened when the first opening 211 is blocked. The casing 21 and the lid portion 214 are formed of, for example, metal or alloy. A principal surface of the lid portion 214 may have an optimal shape such as a rectangular shape or a polygonal shape considering a flow of the air inside the casing 21. Alternatively, a magnet may be provided in an end portion of the lid portion 214 placed in the side where the lid portion 214 is opened, so that the magnet is attached to the casing 21 while the lid portion 214 is closed. When the magnet is provided in the lid portion 214, a magnetic force of this magnet is set sufficient to open the lid portion 214 when the first opening 211 is blocked.

The air blower 22 is placed in the vicinity of the second opening 212 relative to the first and third openings 211 and 213. That is, a distance from the air blower 22 to the second opening 212 is smaller than a distance from the first and third openings 211 and 213 to the second opening 212. In the normal state of FIG. 2, the air blower 22 blows the air from the first opening 211 to the second opening 212 (refer to the bold line of FIG. 2). As a result, the heat generated from the control unit 23 is emitted to the outside to suppress a temperature increase inside the casing 21. The air blower 22 includes, for example, a fan.

The control unit 23 is placed between the air blower 22 and the second opening 212. The control unit 23 includes a central processing unit (CPU), a field programmable gate array (FPGA), and the like having a plurality of electronic parts to control the operation of the surgical microscope 1. For example, the control unit 23 determines opening or closing of the lid portion 214 based on a detection result of the detection unit 24 and controls the output unit 25 based on a result of the determination. The electronic parts include, for example, an integrated circuit (IC) such as a large scale integration (LSI) circuit. Such electronic parts generate heat during the operation, but the heat is cooled by the air blowing from the air blower 22.

The detection unit 24 is placed on the bottom surface of the casing 21 in the side where the lid portion 214 is opened to detect an open/close state of the lid portion 214. The detection unit 24 includes, for example, an infrared distance sensor to detect a distance to the lid portion 214 using reflection light of the infrared ray with which the lid portion 214 is irradiated. A distance when the lid portion 214 is opened is detected to be larger than a distance when the lid portion 214 is closed. Alternatively, when a magnet is provided in the lid portion 214, a magnetic sensor may be provided in the detection unit 24 to detect an intensity of the magnetic field.

The output unit 25 outputs information regarding blockage of the first opening 211 (blockage information) under control of the control unit 23 depending on a detection result of the detection unit 24. The output unit 25 may have, for example, a loudspeaker that outputs the blockage information of the first opening 211 as voice or a lamp that outputs the blockage information as bright light or flickering light. In addition, the output unit 25 may also function as an interface that outputs the blockage information to the display device. The display device that obtains the blockage information output from the output unit 25 displays the blockage information. Alternatively, the blockage information herein may contain information for informing blockage of the first opening 211 or information for prompting checking or solving the cause of the blockage.

Figure 3:
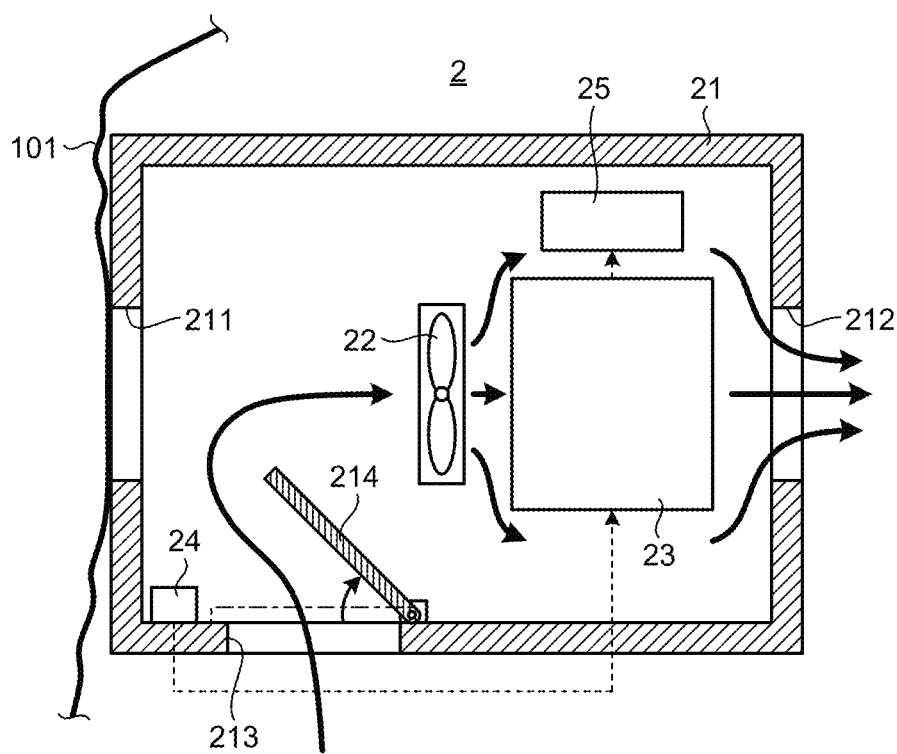
FIG. 3 is a diagram illustrating an internal situation of the base portion when a first opening is blocked.

FIG. 3 is a diagram illustrating an internal situation of the base portion 2 while the first opening 211 is blocked. Since the side wall provided with the first opening 211 is a side wall placed in the side facing a medical examinee body as described above, the side wall may be covered by a clean cover cloth 101 as illustrated in FIG. 3. In this state, the air does not flow from the first opening 211 which is blocked, and a negative pressure is generated inside the casing 21 due to a pressure decrease caused by suctioning of the air blower 22. When this negative pressure is generated, the lid portion 214 is opened so that the air flows from the third opening 213 to the base portion 2 as illustrated in FIG. 3 (refer to the bold line of FIG. 3). That is, when the first opening 211 is blocked, the air flows to the inside of the base portion 2 through a backup suctioning path by setting the third opening 213 as an inlet duct.

The control unit 23 determines that the lid portion 214 is opened based on the detection result of the detection unit 24 and performs control for allowing the output unit 25 to output the blockage information. As a result, a user may be notified of the blockage of the first opening 211.

According to the first embodiment described above, the lid portion 214 of the casing 21 may be opened by virtue of the negative pressure of the base portion 2 generated when the first opening 211 is blocked. When the control unit 23 determines that the lid portion 214 is opened based on the detection result of the detection unit 24, the output unit 25 outputs the blockage information of the first opening 211 to the outside. Therefore, any high-performance temperature detection mechanism or heat radiation means is not necessary. Therefore, using a simple and inexpensive configuration, it is possible to accurately determine blockage of the inlet duct and prevent abnormality in the operation. Furthermore, it is possible to accurately provide notification of blockage of the inlet duct.

According to the first embodiment, the lid portion 214 is opened to the side where the first opening 211 is placed. Therefore, even when the lid portion 214 is opened, and the air flows from the third opening 213, the air reaches the air blower 22 through the same path as that of a case where the air flows from the first opening 211. Therefore, even when the first opening 211 is blocked, it is possible to obtain a heat radiation effect similar to that of a case where the first opening 211 is not blocked.

According to the first embodiment, the lid portion 214 is opened even when the first opening 211 is blocked. Therefore, it is possible to suppress degradation of air suctioning efficiency and prevent a high temperature from being abnormally generated from the inside of the base portion 2. Therefore, it is possible to maintain heat radiation efficiency.

According to the first embodiment, a user may monitor whether or not there is blockage of the first opening 211 in a real-time manner.

According to the first embodiment, the backup suctioning path is closed in a normal state. Therefore, it is possible to improve a degree of freedom in a layout of the third opening 213.

Second Embodiment

Figure 4:
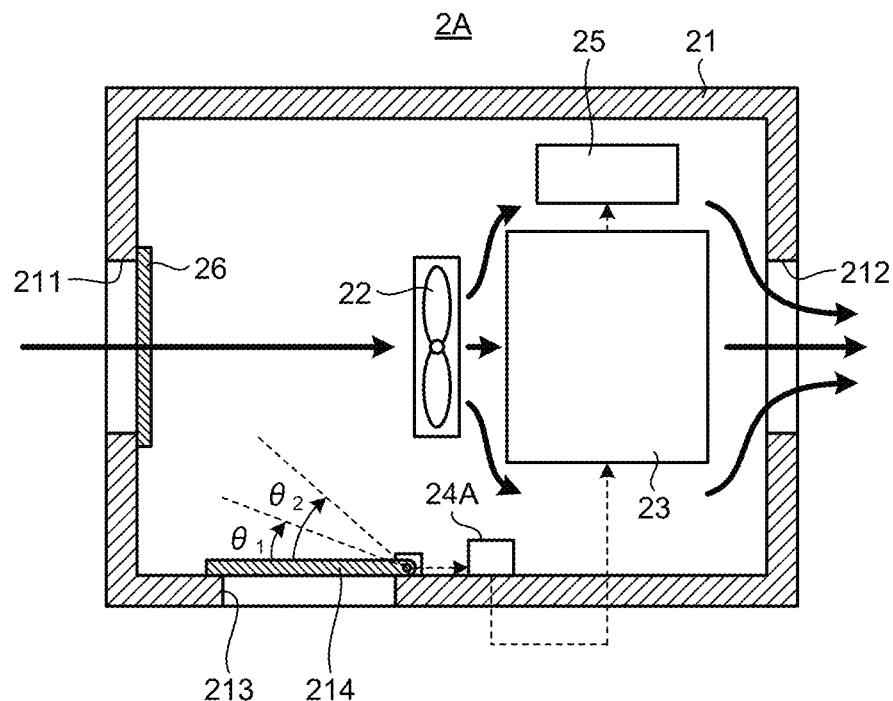
FIG. 4 is a diagram illustrating a schematic internal configuration of a base portion provided in a medical electronic apparatus according to a second embodiment.

FIG. 4 is a diagram illustrating a schematic internal configuration of a base portion provided in a surgical microscope as a medical electronic apparatus according to a second embodiment. In FIG. 4, the base portion 2A has a casing 21, an air blower 22, a control unit 23, a detection unit 24A, an output unit 25, and a filter 26. A configuration of the surgical microscope excluding the base portion 2A is similar to that of the surgical microscope 1 described in the first embodiment.

The detection unit 24A has an angular sensor for detecting an opening angle of the lid portion 214. Alternatively, a rotational sensor for detecting rotation of the lid portion 214 may also be employed as the detection unit 24A. In addition, the infrared distance sensor or the magnetic sensor described in the first embodiment may also be employed, and the control unit 23 may perform calculation for converting the detection result into a rotation angle of the lid portion 214.

The filter 26 covers an inner circumferential side of the first opening 211 to absorb dust or dirt contained in the air flowing from the first opening 211 and prevents intrusion of dust or dirt to the inside of the casing 21. The filter 26 includes, for example, non-woven fabrics.

If the filter 26 is used for a long time, clogging occurs in the filter 26, so that a ventilation air amount of the filter 26 is reduced depending on a degree of clogging. In order to compensate for the reduced suctioning air amount of the air blower 22 generated by this reduction of the ventilation air amount, the lid portion 214 is opened, and the air is supplied from the third opening 213. An opening angle of the lid portion 214 in this state is smaller than an opening angle of the lid portion 214 when the first opening 211 is blocked. Therefore, according to the second embodiment, it is necessary to distinguish a state in which the lid portion 214 is opened due to clogging of the filter 26 and a state in which the lid portion 214 is opened due to blockage of the first opening 211.

In this regard, according to the second embodiment, a range of the opening angle $\theta$ for allowing the control unit 23 to determine that the filter 26 is clogged relative to the opening angle $\theta$ of the lid portion 214 detected by the detection unit 24A is set to $\theta_1 \leq \theta < \theta_2$ (where $\theta_1 < \theta_2$) in advance. In addition, a range of the opening angle $\theta$ for allowing the control unit 23 to determine blockage of the first opening 211 is set to $\theta \geq \theta_2$ in advance. If the opening angle $\theta$ detected by the detection unit 24A has a range of $\theta_1 \leq \theta < \theta_2$, the control unit 23 determines that the filter 26 is clogged and allows the output unit 25 to output information regarding clogging of the filter 26 (clogging information). The clogging information herein contains information for informing that the filter 26 is clogged or information for prompting replacement of the filter 26. Meanwhile, if the opening angle $\theta$ detected by the detection unit 24A has a range of $\theta \geq \theta_2$, the control unit 23 allows the output unit 25 to output the blockage information of the first opening 211.

According to the second embodiment described above, it is possible to obtain the same effects as those of the first embodiment. In addition, according to the second embodiment, since the filter 26 is installed in the first opening 211, it is possible to reliably prevent intrusion of dust or dirt into the inside of the base portion 2.

According to the second embodiment, it is possible to provide notification of blockage of the first opening 211 and clogging of the filter 26 as different states. Therefore, a user may be distinguishably notified of the two states and appropriately respond to each state.

Alternatively, the range of the opening angle $\theta$ may be further subdivided, so that notification of the degree of clogging of the filter 26 is provided in different levels. For example, a state in which clogging occurs in the filter 26, but replacement is not necessary and a state in which clogging occurs in the filter 26, and replacement is immediately necessary may be distinguishably determined. In this case, an upper limit value of the opening angle $\theta$ for a state in which replacement is not necessary is smaller than a lower limit value of the opening angle $\theta$ for a state in which replacement is necessary.

Modification of Second Embodiment

Figure 5:
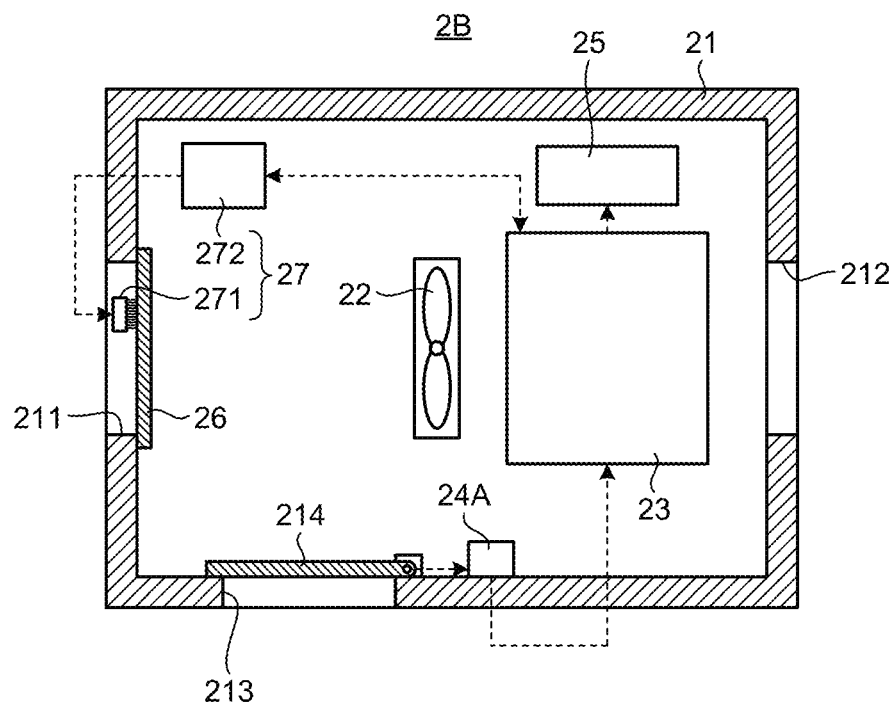
FIG. 5 is a diagram illustrating a schematic internal configuration of the base portion provided in the medical electronic apparatus according to a modification of the second embodiment.

FIG. 5 is a diagram illustrating a schematic internal configuration of a base portion provided in a surgical microscope as a medical electronic apparatus according to a modification of the second embodiment. In FIG. 5, the base portion 2B has a remover 27 for removing clogging of the filter 26 in addition to the configuration of the base portion 2A described above.

The remover 27 has a brush portion 271 for removing adhered substances such as dust or dirt adhered to the surface by sweeping the surface of the first opening 211 side of the filter 26 and a brush actuator 272 for actuating the brush portion 271 under control of the control unit 23. Alternatively, a reservoir for storing the adhered substances removed by the brush portion 271 may be provided in the vicinity of the brush portion 271.

According to this modification, when the opening angle $\theta$ of the lid portion 214 detected by the detection unit 24A has a range of $\theta_1 \leq \theta < \theta_2$, the control unit 23 actuates the brush actuator 272 to allow the brush portion 271 to remove clogging of the filter 26.

Alternatively, the operation of the remover 27 may start in response to a user input from a predetermined input unit. In this case, it is possible to prevent the remover 27 from being operated, for example, during surgical operation. In addition, whether the remover 27 is automatically or manually operated in response to a detection result of the detection unit 24A may be selectably set.

According to the modification of the second embodiment described above, it is possible to remove clogging of the filter 26 in addition to the effects similar to those of the second embodiment.

Alternatively, without limiting the configuration of the remover 27 to those described above, for example, a roll-shaped filter may be provided, so that a new filter surface may be placed in the first opening 211 by winding the filter when clogging of the filter is detected.

Third Embodiment

Figure 6:
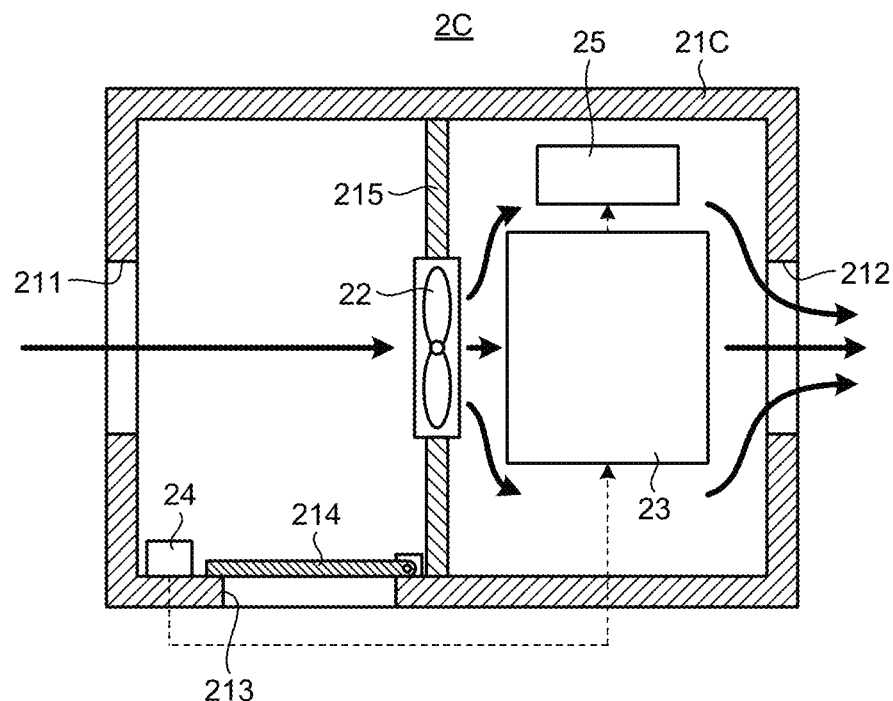
FIG. 6 is a diagram illustrating a schematic internal configuration of a base portion provided in a medical electronic apparatus according to a third embodiment.

FIG. 6 is a diagram illustrating a schematic internal configuration of a base portion provided in a surgical microscope as a medical electronic apparatus according to a third embodiment. In FIG. 6, the base portion 2C has a casing 21C, an air blower 22, a control unit 23, a detection unit 24, and an output unit 25. A configuration of the surgical microscope excluding the base portion 2C is similar to that of the surgical microscope 1 described in the first embodiment.

The casing 21C has a partitioning wall 215 for partitioning upstream and downstream sides of the air blower 22 in addition to the configuration of the casing 21 described in the first embodiment. The upstream side space of the partitioning wall 215, that is, a space between the first opening 211 and the air blower 22 and provided with the lid portion 214 in its bottom is preferably sealed with a sealing member or the like excluding the first and third openings 211 and 213. As a result, a time until the lid portion 214 is opened in response to blockage of the first opening 211 is reduced. In addition, as a volume of the upstream side space of the partitioning wall 215 becomes smaller, the time until the lid portion 214 is opened in response to blockage of the first opening 211 is reduced, which is further preferable.

According to the third embodiment described above, it is possible to obtain the same effects as those of the first embodiment. In addition, according to the third embodiment, the casing 21C has the partitioning wall 215. Therefore, when the first opening 211 is blocked, airtightness is high in the upstream side of the air blower 22, and a negative pressure is generated to be higher than that of the casing 21 of the first embodiment. Therefore, the lid portion 214 is opened more rapidly in response to blockage of the first opening 211, so that it is possible to more reliably prevent an increase of the internal temperature of the base portion 2C caused by blockage of the first opening 211.

Fourth Embodiment

Figure 7:
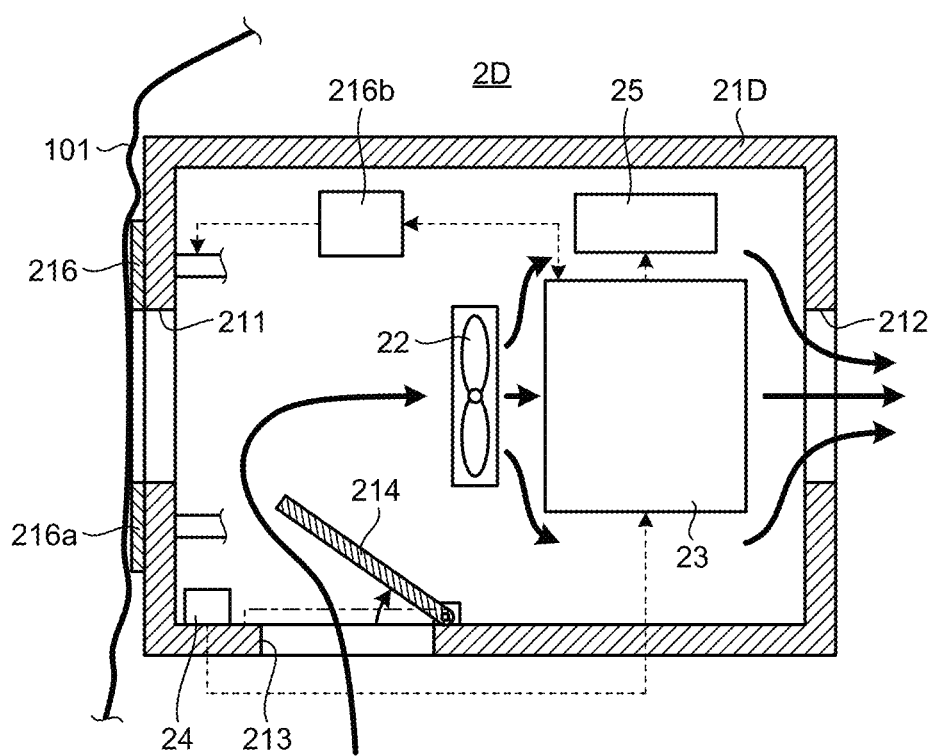
FIG. 7 is a diagram illustrating a schematic internal configuration of a base portion provided in a medical electronic apparatus according to a fourth embodiment.

FIG. 7 is a diagram illustrating a schematic internal configuration of a base portion provided in a surgical microscope as a medical electronic apparatus according to a fourth embodiment. In FIG. 7, the base portion 2D has a casing 21D, an air blower 22, a control unit 23, a detection unit 24, and an output unit 25. A configuration of the surgical microscope excluding the base portion 2D is similar to that of the surgical microscope 1 described in the first embodiment.

The casing 21D has a blockage release portion 216 for releasing blockage of the first opening 211 in addition to the configuration of the casing 21 described in the first embodiment. The blockage release portion 216 is provided in the side wall where the first opening 211 is provided and has an arm portion 216a that advances or retreats in a direction perpendicular to an outer surface of the side wall and an arm actuator 216b for actuating the arm portion 216a under control of the control unit 23.

As the lid portion 214 is opened as the first opening 211 is blocked by the cover cloth 101 as illustrated in FIG. 7, the control unit 23 determines that the first opening 211 is blocked based on the detection result of the detection unit 24. Subsequently, the control unit 23 operates the arm actuator 216b to allow the arm portion 216a to protrude outward, so as to release blockage of the first opening 211 caused by the cover cloth 101.

Figure 8:
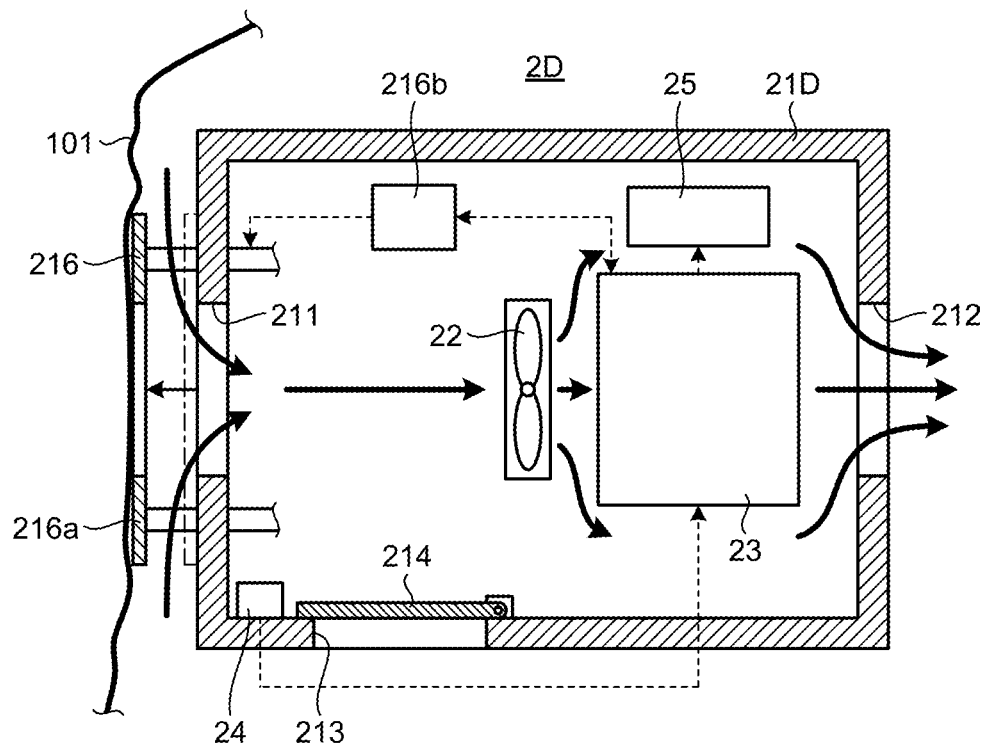
FIG. 8 is a diagram illustrating a state in which blockage of the first opening is released by protruding an arm portion.

FIG. 8 is a diagram illustrating a state in which blockage of the first opening 211 is released by protruding the arm portion 216a. In this state, the lid portion 214 is closed and returns to an initial position where the third opening 213 is covered.

According to the fourth embodiment described above, it is possible to obtain the same effects as those of the first embodiment. In addition, according to the fourth embodiment, since the blockage release portion 216 is provided, it is possible to automatically release a blockage state when the first opening 211 is blocked.

Fifth Embodiment

Figure 9:
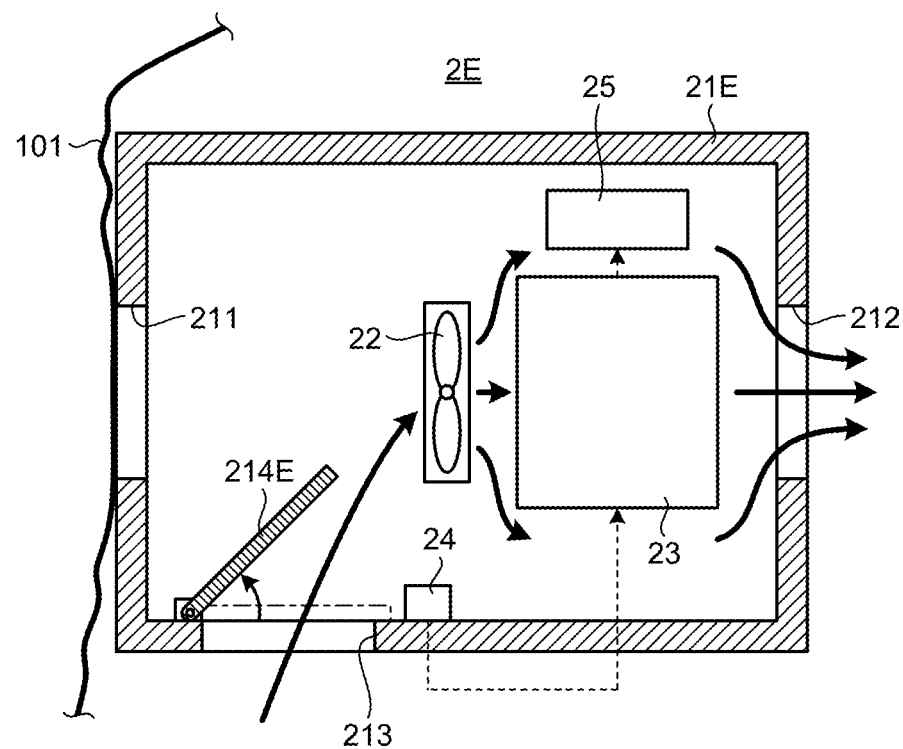
FIG. 9 is a diagram illustrating a schematic internal configuration of a base portion provided in a medical electronic apparatus according to a fifth embodiment.

FIG. 9 is a diagram illustrating a schematic internal configuration of a base portion provided in a surgical microscope as a medical electronic apparatus according to a fifth embodiment. In FIG. 9, the base portion 2E has a casing 21E, an air blower 22, a control unit 23, a detection unit 24, and an output unit 25. A configuration of the surgical microscope excluding the base portion 2E is similar to that of the surgical microscope 1 described in the first embodiment.

In the casing 21E, an opening direction of the lid portion 214 is different from that of the casing 21 of the first embodiment. The lid portion 214 is opened to the side where the air blower 22 is placed. Accordingly, the detection unit 24 that detects opening or closing of the lid portion 214E is placed in the bottom surface of the downstream side of the lid portion 214E. A configuration of the base portion 2E excluding this arrangement is similar to that of the base portion 2 of the first embodiment.

According to the fifth embodiment described above, the lid portion 214E is opened toward the side of the air blower 22 (downstream side of the air flow). Therefore, when the first opening 211 is blocked, the path of the air from the third opening 213 to the air blower 22 is short. For this reason, the time until a negative pressure is released in response to opening of the lid portion 214E is reduced. It is possible to obtain the same effects as those of the first embodiment in other parts of the first embodiment.

Sixth Embodiment

Figure 10:
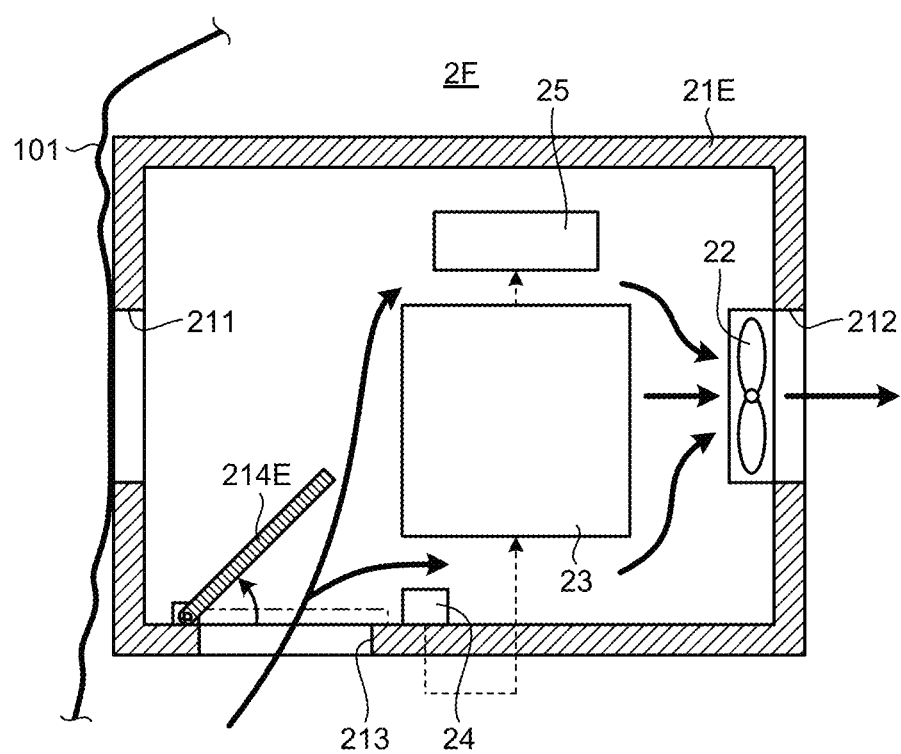
FIG. 10 is a diagram illustrating a schematic internal configuration of a base portion provided in a medical electronic apparatus according to a sixth embodiment.

FIG. 10 is a diagram illustrating a schematic internal configuration of a base portion provided in a surgical microscope as a medical electronic apparatus according to a sixth embodiment. In FIG. 10, the base portion 2F has a casing 21E, an air blower 22, a control unit 23, a detection unit 24, and an output unit 25. A configuration of the surgical microscope excluding the base portion 2F is similar to that of the surgical microscope 1 described in the first embodiment.

The air blower 22 is provided in the inner side of the second opening 212. The control unit 23 is placed in the vicinity of the downstream side of the lid portion 214E. In this configuration, when the first opening 211 is blocked, and the lid portion 214E is opened, the air suctioning from the third opening 213 directly reaches the control unit 23. Therefore, it is possible to rapidly cool the control unit 23. Alternatively, the air blower 22 may be separated from the second opening 212.

According to the sixth embodiment described above, it is possible to obtain the same effects as those of the first embodiment. In addition, according to the sixth embodiment, the control unit 23 is placed in the vicinity of the side where the lid portion 214E is opened. Therefore, it is possible to rapidly cool the control unit 23 when the lid portion 214E is opened. In addition, it is possible to obtain high heat radiation efficiency.

Other Embodiments

While embodiments have been described hereinbefore, it would be appreciated that the disclosure is not limited to the first to sixth embodiments described above. For example, the lid portion may be formed of a flexible sheet-like material. In addition, the lid portion may be substituted with an openable/closable valve that is opened when a negative pressure is generated in the inside of the base portion. In addition, by providing an elastic member such as a spring for biasing the lid portion toward a lid portion closing direction, it is possible to rapidly close the lid portion when the negative pressure inside the base portion is released. Alternatively, the elastic member may be formed of any material that may exert an elastic force sufficient not to close the lid portion when a negative pressure is generated in the inside of the base portion, and the lid portion is opened.

In the third to sixth embodiments, a filter 26 may be installed in the first opening 211 as in the second embodiment. In addition, a filter may be installed in the third opening 213 as well.

In the second and fourth to sixth embodiments, a partitioning wall 215 may be provided in the base portion as in the third embodiment.

The second opening 212 may have a variable opening area that may change under control of the control unit 23. In addition, control may be performed such that the opening area of the second opening 212 increases when the control unit 23 determines blockage of the first opening 211.

The number of the air blowers 22 may not be singular. For example, an inlet air blower may be provided in the vicinity of the first opening 211, and an outlet air blower may be provided in the vicinity of the second opening 212. Furthermore, the number of the inlet ducts and the number of the outlet ducts may also be set differently as appropriate.

The control unit 23 may control the rotation number of the fan of the air blower 22. In this case, a means for detecting the rotation number of the fan is provided to control the rotation number under control of the control unit 23. For example, the control unit 23 may perform control such that the rotation number of the air blower 22 increases when the control unit 23 determines blockage of the first opening 211.

The medical electronic apparatus may be, for example, an endoscope system provided with an endoscope inserted into a medical examinee body to capture the inside of the medical examinee body. In this case, the aforementioned configuration may be applied to a processing unit (also referred to as a camera control unit) for processing images captured by the endoscope and controlling the endoscope system.

According to the present disclosure, it is possible to perform accurate processing and provide notification of occurrence of abnormality using a simple configuration when the air inlet duct is blocked.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical electronic apparatus, comprising:
a casing including a lid provided with: a first inlet duct; a second inlet duct; and an outlet duct, the lid to open the second inlet duct when the first inlet duct is blocked, wherein the first inlet duct and the outlet duct are in side walls of the casing, and the second inlet duct is in a bottom portion of the casing;
a sensor to detect an open/close state of the lid; and
a circuit configured to output information regarding blockage of the first inlet duct by a cloth based on a detection result of the sensor.

2. The medical electronic apparatus according to claim 1, wherein the lid openably/closably covers the second inlet duct.

3. The medical electronic apparatus according to claim 1, further comprising an air blower to blow air flowing from the first or second inlet duct to the outlet duct.

4. The medical electronic apparatus according to claim 1, wherein the circuit is further configured to
determine the open/close state of the lid based on the detection result of the sensor, and
output information regarding blockage of the first inlet duct when the lid is opened.

5. The medical electronic apparatus according to claim 1, wherein the lid opens toward a side where the first inlet duct is placed.

6. The medical electronic apparatus according to claim 1, wherein the circuit is to determine the open/close state of the lid based on the detection result of the sensor, and
a blockage release portion to release blockage of the first inlet duct when the circuit determines that the lid is opened.

7. The medical electronic apparatus according to claim 1, further comprising an air blower, the air blower being closer to the outlet duct than to the first inlet duct and to the second inlet duct.

8. The medical electronic apparatus according to claim 1, further comprising an air blower, wherein, on condition that the open state of the lid is detected, the circuit is configured to increase a number of rotations of the air blower.

9. The medical electronic apparatus according to claim 1, wherein the first inlet duct is a first opening.

10. The medical electronic apparatus according to claim 1, further comprising an air blower to blow air flowing from the first or second inlet duct to the outlet duct,
wherein the lid opens toward a side where the air blower is provided.

11. The medical electronic apparatus according to claim 10, wherein the sensor is on the bottom portion of the casing to determine the open/close state.

12. The medical electronic apparatus according to claim 1, further comprising an air blower to blow air flowing from the first or second inlet duct to the outlet duct,
wherein the casing includes a partitioning wall to partition a space between the first inlet duct and the air blower and provided with a bottom surface where the lid is located.

13. The medical electronic apparatus according to claim 12, wherein a space between the first inlet duct and the air blower and provided with the bottom surface where the lid is placed is hermetically sealed excluding areas where the first and second inlet ducts and the air blower are provided.

14. The medical electronic apparatus according to claim 1, further comprising a filter installed in the first inlet duct to absorb dust or dirt.

15. The medical electronic apparatus according to claim 14, the circuit is configured to:
determine whether the lid is open due to clogging in the filter or due to blockage of the cloth, and
output information regarding clogging on condition that the clogging occurs in the filter.

16. The medical electronic apparatus according to claim 15, further comprising a brush that clears blockage of the first inlet duct when the circuit determines that clogging occurs in the filter.

17. A medical electronic apparatus, comprising:
a casing including a first inlet duct, a second inlet duct, an outlet duct, and a lid covering the second inlet duct, the lid to open the second inlet duct when the first inlet duct is blocked by a cloth, wherein the first inlet duct and the outlet duct are in side walls of the casing, and the second inlet duct is in a bottom portion of the casing;

an air blower; and a circuit configured to detect an open/close state of the lid, output information regarding blockage of the first inlet duct by the cloth based on the state of the lid, and on condition that the open state of the lid is detected, increase a number of rotations of the air blower.

18. The medical electronic apparatus according to claim 17, wherein the first inlet duct is fully open.

19. The medical electronic apparatus according to claim 18, further comprising a blockage release portion to release blockage of the first inlet duct when the circuit determines that the lid is opened.

* * * * *